United States Patent
Konieczna et al.

(10) Patent No.: US 7,955,621 B2
(45) Date of Patent: Jun. 7, 2011

(54) PHARMACEUTICAL FORMULATION COMPRISING LEVOTHYROXINE SODIUM

(75) Inventors: Malgorzata Konieczna, Poznan (PL); Heiner Krohn, Bad Oldesole (DE); Wanda Roman, Poznan (PL); Hendrik Schlehahn, Bad Oldesloe (DE); Malgorzata Anna Strozyk, Poznan (PL)

(73) Assignee: Aspen Global Incorporated, Port Louis (MU)

( * ) Notice: Subject to any disclaimer, the term of this patent is extended or adjusted under 35 U.S.C. 154(b) by 131 days.

(21) Appl. No.: 10/564,148

(22) PCT Filed: Jul. 8, 2004

(86) PCT No.: PCT/EP2004/007667
§ 371 (c)(1),
(2), (4) Date: Nov. 9, 2006

(87) PCT Pub. No.: WO2005/004849
PCT Pub. Date: Jan. 20, 2005

(65) Prior Publication Data
US 2007/0110803 A1 May 17, 2007

(30) Foreign Application Priority Data
Jul. 10, 2003 (GB) .................................. 0316206.2

(51) Int. Cl.
*A61K 31/198* (2006.01)
(52) U.S. Cl. ........................................ 424/465; 514/567
(58) Field of Classification Search .................... 424/465
See application file for complete search history.

(56) References Cited

U.S. PATENT DOCUMENTS

| 5,955,105 A * | 9/1999 | Mitra et al. ................... 424/464 |
| 5,958,979 A | 9/1999 | Lahr et al. |
| 5,976,600 A * | 11/1999 | Ruszkay et al. .............. 426/518 |
| 6,190,696 B1 | 2/2001 | Groenewoud |
| 6,555,581 B1 | 4/2003 | Franz et al. |
| 2003/0032675 A1 * | 2/2003 | Franz et al. .................... 514/567 |

FOREIGN PATENT DOCUMENTS

| JP | 11-286456 | 10/1999 |
| JP | 2001-064177 | 3/2001 |
| JP | 2001-163770 | 6/2001 |
| WO | WO95/20954 | 8/1995 |
| WO | WO01/74448 | 10/2001 |

OTHER PUBLICATIONS

European (European Pharmacopoeia (2002) p. 1438).*
Handbook (Handbook of Pharmaceutical Excipients: 5th edition. p. 134, 725 and 731 (2006)).*
MSDS (Material Safety Data Sheet: L-Thyroxine, sodium salt).*
Handbook (Handbook of Pharmaceutical Excipients: 5th edition. p. 732 (2006)).*
Hager's Handbuch de Pharmazeutischen Praxis, 5., vollständig neubearbeitete Auflage, Springer-Verlag Berlin Heidelberg pp. 733-734, 1993.
Rolski, Chemia Srodkow Lecznichzych, str. 654-655, PZWL, Warszawa 1968.
Iskandarani et al. "Scale-up feasibility in high-shear mixers: Determination through statistical procedures" Drug Dev. and Industr. Pharm. 27:651-657 (2001).

* cited by examiner

*Primary Examiner* — Jake M. Vu
(74) *Attorney, Agent, or Firm* — Nixon & Vanderhye P.C.

(57) ABSTRACT

There is provided a stable pharmaceutical formulation comprising (a) an effective amount of levothyroxine sodium, (b) microcrystalline cellulose which has a mean particle size of less than 125 μm and is present in an amount of 60 to 85% w/w based upon the total weight of the formulation, and (c) pregelatinised starch present in an amount of 5 to 30% w/w based upon total weight of the formulation. There is also provided a process for the preparation of such a formulation.

2 Claims, No Drawings

PHARMACEUTICAL FORMULATION COMPRISING LEVOTHYROXINE SODIUM

CROSS-REFERENCE TO RELATED APPLICATIONS

This application is filed pursuant to 35 USC 371 as a United States National Phase Application of International Patent Application Serial No. PCT/EP2004/007667 filed on Jul. 8, 2004, which claims priority from 0316206.2 filed on Jul. 10, 2003 in the United Kingdom.

FIELD OF THE INVENTION

The present invention relates to stable pharmaceutical formulations of levothyroxine sodium, useful in the treatment of thyroid hormone disorders in mammals, including humans. The invention also relates to a process for preparing such a formulation.

BACKGROUND OF THE INVENTION

Levothyroxine sodium is widely used in the treatment and/or prophylaxis of thyroid hormone disorders. Levothyroxine sodium is presently commercially available under the trademark Eltroxin™ in the form of 50 µg and 100 µg tablets. These tablets contain levothyroxine sodium, lactose, magnesium stearate, acacia powder, sodium citrate and maize starch. Whilst levothyroxine sodium is relatively stable in pure form, pharmaceutical formulations containing levothyroxine sodium exhibit a relatively short shelf life, particularly under conditions of high light, heat, air and humidity (see "Kinetics of Degradation of Levothyroxin Sodium in Aqueous solution and in Solid State", Chong Min Won, Pharmaceutical Research, Vol. 9, No 1, (1992), 131-137). The present Invention is therefore directed at providing a stable solid dosage form of levothyroxine sodium. It is also desired that the solid dosage form disintegrates rapidly, thereby ensuring rapid release of the active ingredient, and is aesthetically acceptable and palatable to the patient.

SUMMARY OF THE INVENTION

The present inventors have found that a pharmaceutical formulation comprising levothyroxine sodium, microcrystalline cellulose with a mean particle size less than 125 µm and pregelatinised starch provides a solid dosage form with improved stability and disintegration characteristics that is aesthetically acceptable and palatable to the patient. Accordingly, the present invention provides a pharmaceutical formulation comprising (a) an effective amount of levothyroxine sodium, (b) microcrystalline cellulose which has a mean particle size of less than 125 µm and is present in an amount of 60 to 85% w/w based upon the total weight of the formulation and (c) pregelatinised starch present in an amount of 5 to 30% w/w based upon total weight of the formulation. The pharmaceutical formulations of the present invention have improved stability such that they are stable to the extent that potency decreases by less than 5%, preferably less than 4%, more preferably less than 3% when the pharmaceutical formulation is stored at 25° C. and 60% relative humidity for 12 months. The pharmaceutical formulations of the present invention have improved disintegration characteristics such that they have a disintegration time of less than 6 minutes, preferably less than 5 minutes, more preferably less than 4 minutes when tested in the disintegration test as described in the Examples section below.

DETAILED DESCRIPTION

The chemical name for levothyroxine sodium is sodium (S)-2-amino-3-[4-(4-hydroxy-3,5-diiodphenoxy)-3,5-diiodophenyl]propionate. Levothyroxine sodium is the monosodium salt of the levo-rotatory isomer of thyroxine. Levothyroxine sodium may exist as one or more polymorphic forms, for example one or more crystalline forms, amorphous forms, phases, solid solutions and/or mixtures thereof. All such forms of levothyroxine sodium and/or mixtures thereof are encompassed by the present invention. Preferably the levothyroxine sodium for use in pharmaceutical formulations of the present invention is in hydrated form. More preferably, the levothyroxine sodium for use in pharmaceutical formulations of the present invention is in the pentahydrate form.

Preferably, the levothyroxine sodium is present in an amount less than 1% w/w based upon the total weight of the formulation, more preferably 0.01-0.30% w/w, even more preferably 0.03-0.25% w/w, most preferably 0.06-0.20% w/w. The minimum amount of levothyroxine sodium can vary, so long as an effective amount is utilised to cause the desired pharmacological effect.

Preferably, the microcrystalline cellulose has a mean particle size of $\leq 100$ µm, more preferably $\leq 75$ µm, even more preferably $\leq 50$ µm. Preferably, the microcrystalline cellulose is selected from microcrystalline cellulose grade 101, 102, or 103, more preferably grade 101 or 102, most preferably grade 101. The term 'Grade 101' as used herein means material with nominal mean particle size 50 µm and moisture content $\leq 5.0\%$ in accordance with the European Pharmacopeia (2002). The term 'Grade 102' as used herein means material with nominal mean particle size 100 µm and moisture content $\leq 5.0\%$ in accordance with the European (2002). The term 'Grade 103' as used herein means material with nominal mean particle size 50 µm and moisture content $\leq 3.0\%$ in accordance with the European (2002). The term 'Grade 200' as used herein means material with nominal mean particle size 180 µm and moisture content $\leq 5.0\%$ In accordance with the European (2002). Preferably the microcrystalline cellulose is sourced from FMC Corporation, JRS Rettenmaier or Sähne (Germany) or Wei Ming (Taiwan), more preferably Wei Ming (Taiwan).

Preferably, the microcrystalline cellulose is present in an amount of 60 to 85% w/w based on the total weight of the formulation, more preferably 65 to 80% w/w, most preferably 70 to 80% w/w.

The term 'pregelatinised starch' as used herein means partially pregelatinised starch typically containing about 5% of free amylose, 15% of free amylopectin and 80% unmodified starch. It is produced by subjecting moistened starch to mechanical pressure in order to rupture some or all of the starch granules and subsequent drying. The resultant material is ground and its moisture content adjusted such that it possesses good flow and compression characteristics. Typical cold water solubility of partially pregelatinised starch, e.g. Starch 1500 (Colorcon) is 10-20%. Pregelatinised starch is further defined in the European Pharmacopea (2002) which is included herein by reference. Preferably, the pregelatinised starch is present in an amount of 5 to 30% w/w based on the total weight of the formulation, more preferably 10 to 30% w/w, most preferably 15 to 25% w/w.

Preferably, the ratio of microcrystalline cellulose:pregelatinised starch is in the range of 2:1 to 15:1, more preferably 2.5:1 to 8:1, most preferably 3:1 to 5:1.

Preferably, the microcrystalline cellulose and pregelatinised starch contain water. Preferably, the water comprises 3-6% w/w based on the total weight of the formulation, more preferably about 4.5% (e.g. 4.5%-5.0%).

Preferably, the pharmaceutical formulation includes one or more glidants/lubricants. Suitable/lubricants for use in the present invention include colloidal silicon dioxide, talc, magnesium stearate, zinc stearate, calcium stearate, sodium stearate fumarate and sodium magnesium lauryl sulphate. Preferably, the glidants/lubricants are selected from one or more of: colloidal silicon dioxide, talc and magnesium stearate.

Preferably, the glidant/lubricant is present in an amount 1-10% of the total weight of the formulation, more preferably 2-9% of the total weight of the formulation, most preferably 3-8% of the total weight of the formulation.

Preferably, talc is present in an amount 1-5% of the total weight of the formulation, more preferably 2-4% of the total weight of the formulation, most preferably 2.5-3.5% of the total weight of the formulation.

Preferably, colloidal anhydrous silica is present in an amount 1-5% of the total weight of the formulation, more preferably 1-3% of the total weight of the formulation, most preferably 1.5-2.5% of the total weight of the formulation.

Preferably, magnesium stearate is present in an amount 0.1-5% of the total weight of the formulation, more preferably 0.5-4% of the total weight of the formulation, most preferably 0.8-1.5% of the total weight of the formulation.

Preferably, the pH of the pharmaceutical formulation is in the range pH 6.8 to 8.2, preferably pH 7.2 to 7.8 when suspended in water in a ratio water:pharmaceutical formulation of 10:1.

The formulations of the invention may, if desired, further include one or more pharmaceutically acceptable excipients. All such excipients must be "pharmaceutically acceptable" in the sense of being compatible with the other ingredients of the formulation and not injurious to the patient. Pharmaceutically acceptable excipients may include colours, flavours e.g. menthol, sweeteners e.g. mannitol, preservatives, stabilisers, antioxidants and any other excipients known to those skilled in the art.

It is to be understood that the present invention covers all combinations of particular and preferred groups described hereinabove.

The present invention provides a pharmaceutical formulation for use in medical therapy, e.g. in the treatment of thyroid hormone disorders in an animal, e.g. a mammal such as a human. Levothyroxine and other thyroid hormones are known to serve as hormone replacement therapy when the thyroid function has been reduced or is completely absent for a variety of disease states, Including, hypothyroidism, myxedema, cretinism and obesity, preferably hypothyroidism.

For each of the above-indicated utilities and indications the amount required of levothyroxine sodium will depend on a number of factors including the severity of the condition to be treated and the identity of the recipient and will ultimately be at the discretion of the attendant physician or veterinarian. Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. In general, however, for each of these utilities and indications, a suitable effective dose will be in the range 1.0 to 6.0 µg per kilogram bodyweight of recipient per day, preferably in the 1.5 to 5.0 µg per kilogram bodyweight per day (unless otherwise indicated, all weights are calculated with respect to the free base active ingredient).

The desired dose is preferably presented as one, two, three or four sub-doses administered at appropriate intervals throughout the day. These sub-doses may be administered in unit dosage forms, for example, containing about 10 to 300 µg, preferably 10-200 µg, more preferably 25-150 µg, of active ingredient per unit dose form, most preferably 50 µg or 100 µg of active ingredient per unit dose form.

For example, a 50 µg tablet may comprise 0.0425-0.0575 mg levothyroxine sodium, 50-60 mg microcrystalline cellulose, 12-17 mg pregelatinised starch, 2-3 mg talc, 1-2 mg colloidal anhydrous silica and 0.5-1 mg magnesium stearate. A 100 µg tablet may comprise 0.085-0.115 mg levothyroxine sodium, 100-120 mg microcrystalline cellulose, 24-34 pregelatinised starch, 4-6 mg talc, 2-4 mg colloidal anhydrous silica and 1-2 mg magnesium stearate.

The pharmaceutical formulation is preferably administered orally and is preferably in the form of a tablet. However, in addition to tablets, the composition according to the present invention may also be administered in the form of capsules, caplets, gelcaps, pills, and any other oral dosage forms known in the pharmaceutical art.

The term "treatment" and derivatives such as "treating" as used herein includes both treatment and prophylaxis. Prophylaxis is relevant in relation to protection against such conditions such as hypothyroidism.

A further aspect of the invention provides a process for preparing a pharmaceutical formulation according to the invention.

The tablet may be prepared either by a wet granulation or by a direct compression process. Preferably a direct compression process is used, e.g. using a conventional high speed rotary press.

Preferably, the pharmaceutical formulation is prepared by making an initial preparation of a triturate of levothyroxine sodium and subsequently incorporating the triturate into the tablet formulation. A triturate of levothyroxine sodium comprises levothyroxine sodium and a suitable carrier, e.g. microcrystalline cellulose, wherein the levothyroxine sodium is present in a greater concentration in the triturate than in the final tablet formulation. Preferably, the triturate comprises 2-3% w/w levothyroxine sodium of total weight of triturate. Preparation using a triturate improves distribution of the low concentration of drug throughout the blend and uniformity in the tablets i.e. homogeneous incorporation.

Preferably, the process comprises the steps of: (a) preparing a triturate of levothyroxine sodium and microcrystalline cellulose, (b) mixing the triturate with the remaining components of the pharmaceutical formulation, and (c) compression.

Levothyroxine sodium can be obtained from the thyroid gland of domesticated animals, or alternatively the hormone can be prepared synthetically. Methods for making active ingredient are disclosed in Hagers Handbuch der pharmazeutischen Praxis,—5., vollst. Neubearb., Bd.8.Stoffe: E-O/F . . . Von Bruchhause; (Hrgs.).Bearb . . . von M. Albinus—1993, Springer-Veriag Berlin Heidelberg 1993, pages 733-734; S. Rolski, Chemia środków leczniczych, str. 654-655, PZWL, Warszawa 1968. The contents of which are incorporated herein by reference.

The formulation may be introduced into a container which is then closed. The container may be sealed, e.g. by LDPE tamper-evident snap fit closures. It may be a single-dose or multi-dose container. The container may be bottles, jars, bags or sachets. Sachets, especially foil sachets (foil-foil blisters), are particularly suitable for single dose packaging. Bottles, particularly high density polyethylene (HDPE) or polypropylene (PP) bottles are particularly suitable for multi-dose packaging.

The following examples illustrate aspects of this invention but should not be construed as the scope of the invention in any way.

EXAMPLES

Example 1

Preparation of Levothwroxine Sodium Tablets (a) Formulation

|  | [kg] |
|---|---|
| Levothyroxine sodium pentahydrate | 0.074 |
| Microcrystalline cellulose | 75.0 |
| Pregelatinised starch | 20.0 |
| Talc | 3.0 |
| Colloidal silicon dioxide | 2.0 |
| Magnesium stearate | 1.0 |

Manufacturing Process

Levothyroxine sodium tablets were manufactured by a direct compression process comprising the following steps:
- preparation of a levothyroxine sodium triturate with a portion of the microcrystalline cellulose by simple blending
- blending the remainder of the microcrystalline cellulose and pregelatinised starch with the levothyroxine sodium triturate to produce a uniform content of active substance;
- addition of the talc, silicon dioxide colloidal and magnesium stearate, followed by blending to prepare a powder mixture;
- compression of levothyroxine sodium tablets at a crushing strength of not less than 3 Kp and a resulting strength of 3.5-10 Kp.

(b) Formulation

|  | [kg] |
|---|---|
| Levothyroxine sodium pentahydrate | 0.074 |
| Microcrystalline cellulose | 75.0 |
| Pregelatinised starch | 20.0 |
| Talc | 3.0 |
| Colloidal silicon dioxide | 2.0 |
| Magnesium stearate | 1.0 |

Manufacturing Process The manufacturing process for Example 1(b) differed from Example 1(a) in that a preblend of the remainder of microcrystalline cellulose and colloidal silicon dioxide was made before blending with the levothyroxine sodium triturate and pregelatinised starch.

Example 2

Stability of Levothyroxine Sodium Tablets

Comparative stability studies of levothyroxine sodium tablets were based on testing of levothyroxine sodium and total impurities contents after storage of tablets at (i) 40° C./75% RH, (ii) 30° C./60% RH, and (iii) 25° C./60% RH. Suitable HPLC methods were applied. Stability was measured in terms of levothyroxine sodium content and total impurities content:

Total impurities contents were determined using the assay method for levothyroxine sodium tablets in the British Pharmacopoeia 2002 with a sample concentration of 50 µg/ml, sample solvent: methanol and 0.02 M aqueous NaOH (1:1), an injection volume of 100 µl and a phase flow rate of 1.5 ml/min.

Levothyroxine sodium contents were determined using the assay method for levothyroxine sodium tablets in the British Pharmacopoeia 2002 using a sample concentration of 50 µg/ml, sample solvent: methanol and 0.02 M aqueous NaOH (1:1) and phase flow rate of 1.5 ml/min.

The results of these stability tests are provided in tables (A) to (C).

Conclusions (A) Stability of Levothyroxine Sodium Tablets

Comparison of Levothyroxine Sodium Tablets Prepared According to Example 1(b) with Eltroxin™ Tablets The data shows that at 3-9 months after storage a higher levothyroxine sodium content is maintained in tablets according to Example 1(b) than in the marketed formulation of Eltroxin™ and total impurities are lower in tablets according to Example 1(b) than in marketed formulation of Eltroxin™.

(B) Stability of Levothyroxine Sodium Tablets

Effect of Microcrystalline Cellulose Particle Size

The data shows that a higher levothyroxine sodium content is maintained and the total impurities are lower when microcrystalline cellulose with a mean particle size of 50 µm or 100 µm compared to 180 µm is used in the levothyroxine sodium formulation.

(C) Stability of Levothyroxine Sodium Tablets

Effect of Water Content

The data shows that a higher levothyroxine sodium content is maintained in tablets after 3 months storage where the initial water content of the tablets is 4.1 or 4.7% compared to 2.4 or 2.7%.

(A) Stability of Levothyroxine Sodium Tablets

Comparison of Levothyroxine Sodium Tablets Prepared According to Example 1(b) with Eltroxin™ Tablets

| Levothyroxine sodium tablets | Tablets strength [μg] | Storage conditions | Levothyroxine Sodium contents [%]* Storage time [months] | | | | | Total impurities contents [%] Storage time [months] | | | | |
|---|---|---|---|---|---|---|---|---|---|---|---|---|
| | | | Initial value | 3 | 6 | 9 | 12 | Initial value | 3 | 6 | 9 | 12 |
| Example 1 (b) | 100 | | 101.0 | | | | | 1.2 | | | | |
| | | 40° C./75% RH | | 94.3 | 90.5 | — | — | | 3.5 | 4.8 | — | — |
| | | 30° C./60% RH | | 100.2 | 98.2 | 96.1 | 94.3 | | 1.7 | 2.8 | 3.3 | 3.8 |
| | | 25° C./60% RH | | 101.6 | 100.6 | 100.7 | 97.7 | | 1.2 | 1.8 | 2.6 | 2.6 |
| Example 1 (b) | 50 | | 101.4 | | | | | 1.1 | | | | |
| | | 40° C./75% RH | | 92.0 | 84.4 | — | — | | 3.8 | 6.1 | — | — |
| | | 30° C./60% RH | | 100.0 | 99.6 | 98.6 | 93.8 | | 2.7 | 2.9 | 3.4 | 3.8 |
| | | 25° C./60% RH | | 99.8 | 102.4 | 101.4 | 98.2 | | 2.1 | 2.5 | 2.7 | 3.2 |
| Eltroxin ™ | 100 | | 98.0 | | | | | 1.2 | | | | |
| | | 40° C./75% RH | | 89.5 | 83.4 | — | — | | 7.5 | 8.9 | — | — |
| | | 30° C./60% RH | | 93.4 | 88.2 | 89.5 | — | | 4.9 | 7.0 | 6.6 | — |
| | | 25° C./60% RH | | 95.7 | 92.7 | 92.1 | — | | 4.5 | 4.8 | 5.4 | — |

*% to declaration
'—' not tested (B) Stability of Levothyroxine Sodium Tablets

Effect of Microcrystalline Cellulose Particle Size on Levothyroxine Sodium Tablets Prepared According to Example 1(b)

| Microcrystalline cellulose grade | Mean particle size [μm] | Storage conditions: 40° C./75% RH | | | | | |
|---|---|---|---|---|---|---|---|
| | | Levothyroxine Sodium contents [%]* Time [weeks] | | | Total impurities contents [%] Time [weeks] | | |
| | | 2 | 8 | 12 | 2 | 8 | 12 |
| 101 | 50 | 99.7 | 98.1 | 98.3 | 0.0 | 2.6 | 2.8 |
| | | 99.6 | 95.6 | 95.4 | 0.6 | 2.3 | 1.6 |
| 102 | 100 | 95.8 | 90.2 | 88.6 | 4.8 | 6.1 | 6.6 |
| | | 96.0 | 90.5 | 86.8 | 2.3 | 5.0 | 5.5 |
| 200 | 180 | 91.6 | 87.5 | 80.9 | 2.1 | 7.7 | — |

*% to initial value (initial value equals 100%)

(C) Stability of Levothyroxine Sodium Tablets

Effect of Water Content on Levothyroxine Sodium Tablets Prepared According to Example 1(b)

| Tablets strength [μg] | Storage conditions | Loss of drying [%] Storage time [months] | | Levothyroxine Sodium contents [%]* Storage time [months] | |
|---|---|---|---|---|---|
| | | Initial value | 3 | Initial value | 3 |
| 100 | | 4.1 | | 100.6 | |
| | 40° C./75% RH | | 5.1 | | 91.6 |
| | 30° C./60% RH | | 5.1 | | 97.3 |
| | 25° C./60% RH | | 4.4 | | 99.5 |
| 100 | | 2.7 | | 99.7 | |
| | 40° C./75% RH | | 2.8 | | 83.0 |
| | 30° C./60% RH | | 2.6 | | 94.3 |
| | 25° C./60% RH | | 2.7 | | 94.5 |
| 50 | | 4.7 | | 101.4 | |
| | 40° C./75% RH | | 5.7 | | 92.0 |
| | 30° C./60% RH | | 5.1 | | 100.0 |
| | 25° C./60% RH | | 4.9 | | 99.8 |
| 50 | | 2.4 | | 100.6 | |
| | 40° C./75% RH | | 1.6 | | 82.0 |
| | 30° C./60% RH | | 1.4 | | 90.1 |
| | 25° C./60% RH | | 1.2 | | 91.6 |

Example 3

Disintegration of Levothyroxine Sodium Tablets

The disintegration of Levothyroxine Sodium tablets prepared according to Example 1(b) was tested according to the British (BP) 2002 (General Monograph for Tablets, Uncoated Tablets, Disintegration Test).

The results ate presented in table (D):

(D) Disintegration of Levothyroxine Sodium Tablets

| Tablets strength [μg] | Storage conditions | Disintegration time [min, s] Storage time [months] | | | | |
|---|---|---|---|---|---|---|
| | | Initial value | 3 | 6 | 9 | 12 |
| 100 | | 0 mins | | | | |
| | 40° C./75% RH | 38 secs | 2 mins 14 secs | 2 mins 00 secs | — | — |
| | 30° C./60% RH | | 0 mins 37 secs | 2 mins 52 secs | 1 mins 26 secs | 0 mins 57 secs |
| | 25° C./60% RH | | 0 mins 36 secs | 1 mins 00 secs | 1 mins 38 secs | 0 mins 53 secs |
| 50 | | 0 mins | | | | |
| | 40° C./75% RH | 31 secs | 1 mins 40 secs | 1 mins 56 secs | — | — |
| | 30° C./60% RH | | 0 mins 33 secs | 0 mins 32 secs | 0 mins 59 secs | 1 mins 49 secs |
| | 25° C./60% RH | | 0 mins 29 secs | 0 mins 46 secs | 0 mins 45 secs | 0 mins 53 secs |

'—' not tested

Conclusion (D) Disintegration of Levothyroxine Sodium Tablets

The data shows that disintegration of tablets prepared according to Example 1(b) is very fast (less than 4 minutes). The pharmacopoeia for uncoated tablets requires disintegration time only less than 15 minutes.

Throughout the specification and the claims which follow, unless the context requires otherwise, the word "comprise" and variations such as "comprises" and "comprising", will be understood to imply the inclusion of a stated integer or step or group of integers but not to the exclusion of any other integer or step or group of integers or steps.

The invention claimed is:

1. A pharmaceutical formulation in unit dose form which is a "50 μg tablet" of active ingredient comprising: 0.0425-0.0575 mg levothyroxine sodium, 50-60 mg microcrystalline cellulose which has a mean particle size of less than 125 μm, 12-17 mg pregelatinised starch which is produced by subjecting moistened starch to mechanical pressure in order to rupture some or all of its starch granules and subsequent drying, 2-3 mg talc, 1-2 mg colloidal anhydrous silica, and 0.5-1.0 mg magnesium stearate.

2. A pharmaceutical formulation in unit dose form which is a "100 μg tablet" of active ingredient comprising: 0.085-0.115 mg levothyroxine sodium, 100-120 mg microcrystalline cellulose which has a mean particle size of less than 125 μm, 24-34 mg pregelatinised starch which is produced by subjecting moistened starch to mechanical pressure in order to rupture some or all of its starch granules and subsequent drying, 4-6 mg talc, 2-4 mg colloidal anhydrous silica, and 1-2 mg magnesium stearate.

* * * * *